US010522891B2

(12) United States Patent
Drouin et al.

(10) Patent No.: US 10,522,891 B2
(45) Date of Patent: Dec. 31, 2019

(54) MILLIMETER-WAVE COUPLER FOR SEMI-CONFOCAL FABRY-PEROT CAVITY

(71) Applicant: California Institute of Technology, Pasadena, CA (US)

(72) Inventors: Brian J. Drouin, Pasadena, CA (US); Adrian Tang, Pasadena, CA (US); Erich T. Schlecht, Pasadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 0 days.

(21) Appl. No.: 16/054,226

(22) Filed: Aug. 3, 2018

(65) Prior Publication Data
US 2019/0044211 A1 Feb. 7, 2019

Related U.S. Application Data

(60) Provisional application No. 62/540,710, filed on Aug. 3, 2017.

(51) Int. Cl.
H01P 5/02 (2006.01)
G01N 22/00 (2006.01)
H01P 3/12 (2006.01)
H01Q 15/02 (2006.01)
G01N 21/00 (2006.01)

(52) U.S. Cl.
CPC ............... H01P 5/02 (2013.01); G01N 21/00 (2013.01); G01N 22/00 (2013.01); H01P 3/12 (2013.01); H01P 3/121 (2013.01); H01Q 15/02 (2013.01)

(58) Field of Classification Search
CPC .............. H01P 5/02; H01P 3/12; G01N 22/00
See application file for complete search history.

(56) References Cited

U.S. PATENT DOCUMENTS

| 2004/0090368 | A1* | 5/2004 | Channabasappa | ..... H01Q 1/523 343/700 MS |
| 2009/0243762 | A1* | 10/2009 | Chen | ..... H01P 1/2088 333/212 |
| 2012/0097850 | A1* | 4/2012 | Darcie | ..... G01J 3/0205 250/340 |
| 2018/0269557 | A1* | 9/2018 | Fangfang | ..... H01P 3/123 |

OTHER PUBLICATIONS

Vision and Voyages for Planetary Science in the Decade 2013-2022, Committee on the Planetary Science Decadal Survey, Space Studies Board Division on Engineering and Physical Sciences, 2011, pp. 1-410, The National Academies Press,Washington, D.C.

(Continued)

Primary Examiner — Hugh Maupin
(74) Attorney, Agent, or Firm — Gates & Cooper LLP

(57) ABSTRACT

A coupler for coupling electromagnetic radiation into a cavity, including a metal layer having a reflective surface and forming a ground plane; and one or more waveguides for gigahertz or terahertz electromagnetic radiation embedded in the metal layer. The waveguides each include two openings in the metal layer exposing a dielectric underneath; and a section of the metal layer between the two openings. A plurality of holes in the metal layer are disposed along a perimeter of the openings so as to shape the electric field of the electromagnetic radiation in a cavity coupled to the coupler.

21 Claims, 12 Drawing Sheets

(56) References Cited

OTHER PUBLICATIONS

Pickett, H.M, et al., "Submillimeter, Millimeter, and Microwave Spectral Line Catalog", J. Quant. Spectrosc. Radiat. Transfer, 1998, pp. 883-890, vol. 60, No. 5.

Muller, H.S.P., et al., "The Cologne Database for Molecular Spectroscopy, CDMS: a useful tool for astronomers and spectroscopists", Journal of Molecular Structure, 2005, pp. 215-227, vol. 742.

Drouin, B.J., et al., "Submillimeter Wave Spectrometry for In-Situ Planetary Science", 2012 IEEE Aerospace Conference, Mar. 2012, pp. 1-4.

Neese, C.F., et al., "Compact Submillimeter/Terahertz Gas Sensor With Efficient Gas Collection, Preconcentration, and ppt Sensitivity", IEEE Sensors Journal, Aug. 2012, pp. 2565-2574, vol. 12, No. 8.

Balle, T.J., et al., "Fabry-Perot cavity pulsed Fourier transform microwave spectrometer with a pulsed nozzle particle source", Review of Scientific Instruments, 1981, pp. 33-45, vol. 52, No. 1.

Gopalsami, N., et al., "Millimeter-wave cavity ringdown spectroscopy", Review of Scientific Instruments, Feb. 2002, pp. 259-262, vol. 73, No. 2.

Clark, R.N, et al., "Fabry-Perot and open resonators at microwave and millimetre wave frequencies, 2-300 GHz", Journal of Physics E: Scientific Instruments, 1982, pp. 9-24, vol. 15.

Meshkov, A.I, et al., "Broadband absolute absorption measurements of atmospheric continua with millimeter wave cavity ringdown spectroscopy", Review of Scientific Instruments, 2005, pp. 083103-1-083103-10, vol. 76.

Nagarajan, S., et al., "Cavity-Based Medium Resolution Spectroscopy (CBMRS) in the THz: A Bridge Between Highand Low-Resolution Techniques for Sensor and Spectroscopy Applications", IEEE Transactions on Terahertz Science and Technology, May 2017, pp. 233-243, vol. 7, No. 3.

Braakman, R., et al., "Principles and promise of Fabry-Perot resonators at terahertz frequencies", Journal of Applied Physics, 2011, pp. 063102-1-063102-11, vol. 109.

Deprince, B.A., et al., "Extending high-finesse cavity techniques to the far-infrared", Review of Scientific Instruments, 2013, pp. 075107-1-075107-10, vol. 84.

Halfen, D.T., et al., "Interstellar Detection of Methyl Isocyanate CH3NCO in Sgr B2(N): A Link From Molecular Clouds to Comets", The Astrophysical Journal Letters, Oct. 10, 2015, pp. 1-8, vol. 812.

\* cited by examiner

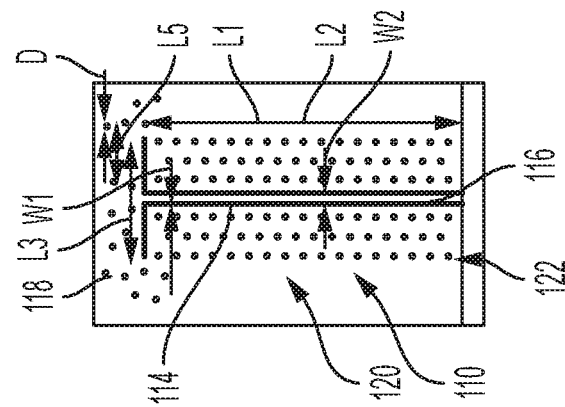
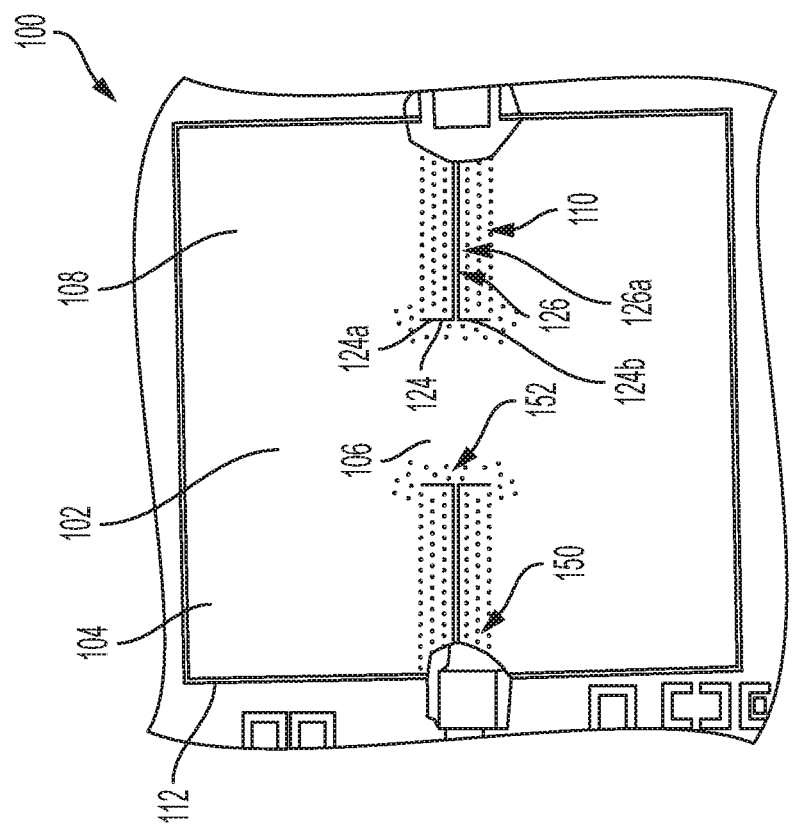
Fig. 1B
Fig. 1A

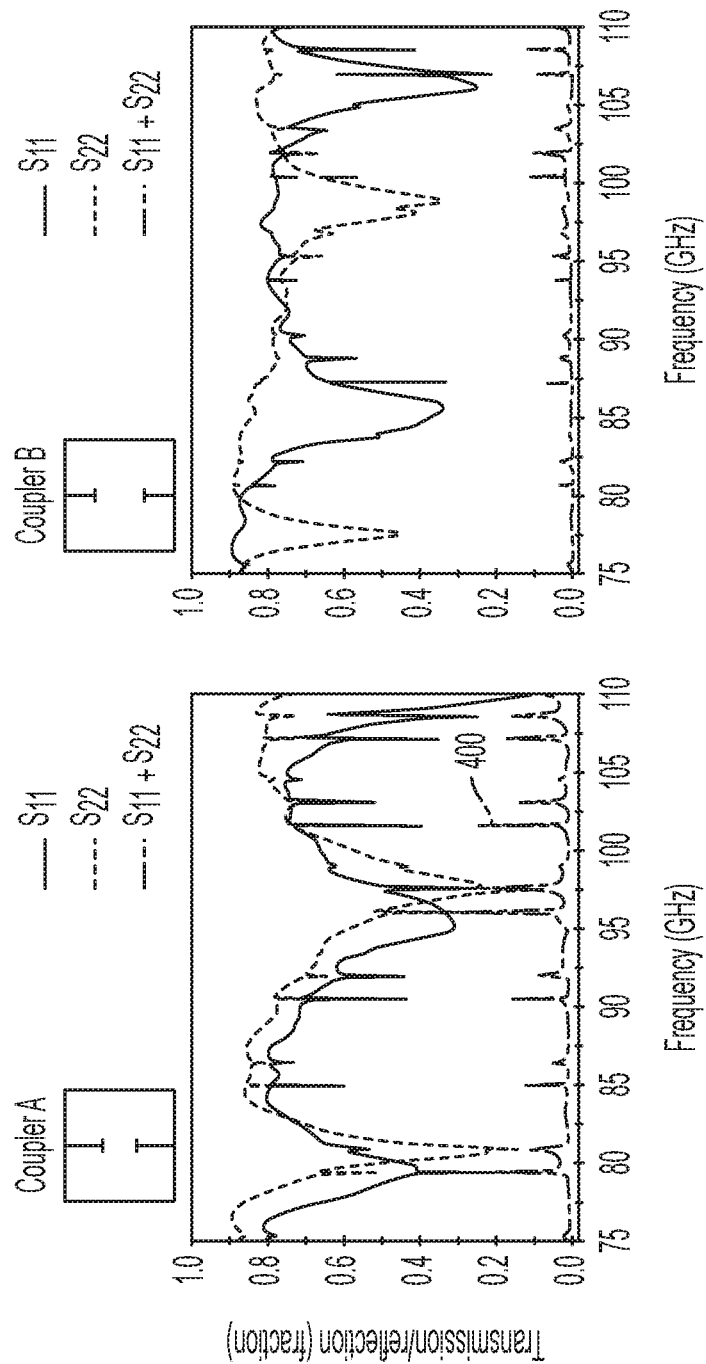

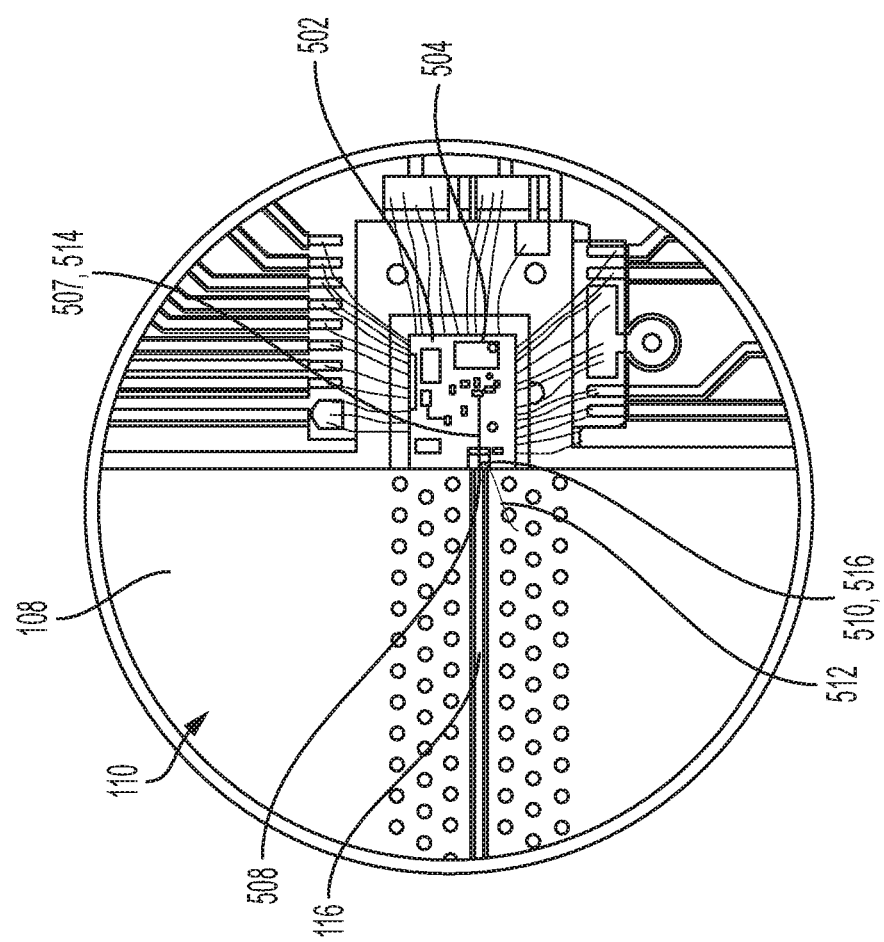

MILLIMETER-WAVE COUPLER FOR SEMI-CONFOCAL FABRY-PEROT CAVITY

CROSS REFERENCE TO RELATED APPLICATIONS

This application claims the benefit under 35 U.S.C. Section 119(e) of commonly-assigned U.S. Provisional Patent Application Ser. No. 62/540,710, filed on Aug. 3, 2017, by Erich T. Schlecht, Adrian J. Tang, Theodore J. Reck, Brian J. Drouin, Deacon J. Nemchick, and Alexander W. Raymond, entitled "MILLIMETER-WAVE COUPLER FOR SEMI-CONFOCAL FABRY-PEROT CAVITY,", which application is incorporated by reference herein.

STATEMENT REGARDING FEDERALLY SPONSORED RESEARCH AND DEVELOPMENT

The invention described herein was made in the performance of work under a NASA contract NNN12AA01C, and is subject to the provisions of Public Law 96-517 (35 USC 202) in which the Contractor has elected to retain title.

BACKGROUND OF THE INVENTION

1. Field of the Invention

This invention relates to a method and system for gas identification and quantification.

2. Description of the Related Art (Note: This application references a number of different publications as indicated throughout the specification by one or more reference numbers within brackets, e.g., [x]. A list of these different publications ordered according to these reference numbers can be found below in the section entitled "References." Each of these publications is incorporated by reference herein.)

Many applications require the detection of small molecular tracers and determination of their abundance and origin. For detections in the gas phase, the rotational spectrum of a polar molecule typically provides a strong interaction with centimeter and shorter wavelength radiation, which has been exploited for remote sensing for half a century with data repositories growing to support the widespread efforts [2,3]. In situ instruments are now being developed [4,5] but have lagged behind remote sensors due to the large equipment traditionally required for generation and detection of this radiation. These first generation instruments are man-portable, but not yet compact enough for many practical applications. Moreover, while cavity resonators have been fabricated for detection in the millimeter [7] and submillimeter [8] range, their use in the millimeter range has been hampered due to difficulties with coupling radiation efficiently into high finesse cavities.

SUMMARY OF THE INVENTION

To overcome the limitations in the art described above, and to overcome other limitations that will become apparent upon reading and understanding this specification, the present disclosure describes a coupler for coupling electromagnetic radiation having a wavelength $\lambda$ (e.g., at band center) into a cavity. The coupler includes a metal layer having a reflective surface, the metal layer forming a ground plane; and one or more waveguides for gigahertz or terahertz electromagnetic radiation embedded in the metal layer.

The waveguides each include two openings in the metal layer exposing a dielectric under the metal layer; and a section of the metal layer between the two openings. A plurality of holes are disposed in the metal layer along an edge of the openings so as to smooth out an electric field of the electromagnetic radiation confined in the cavity.

The coupler can be embodied in many ways including, but not limited to, the following examples.

1. The coupler wherein the holes are disposed around a perimeter of the waveguide.

2. The coupler wherein the holes are disposed in a hexagonal pattern.

3. The coupler of one or any combination of the previous examples wherein the holes have a diameter or a width in a range of $\lambda/15$-$\lambda/5$ or 200-600 micrometers.

4. The coupler of one or any combination of the previous examples wherein the holes are separated by a distance in a range of $\lambda/5$-$\lambda/2$ or 600-1500 micrometers (distance from a center of one hole to a center of an adjacent hole)

5. The coupler of one or any combination of the previous examples wherein the holes are disposed in 2-4 rows.

6. The coupler of one or any combination of the previous examples, wherein the openings in the waveguide have a width in a range of $\lambda/5$-$\lambda/2$, where $\lambda$ is the wavelength at band center, or 600-1500 micrometers in the demonstration.

7. The coupler of one or any combination of the previous examples, wherein the openings each have an L shape having a base portion and a back portion.

8. The coupler of example 7, wherein the base portion has a length in a range of $\lambda/2$-$4\lambda$, or 1-4 mm and the back portion has a length in a range of $3\lambda$-$15\lambda$, or 5-15 millimeters (mm).

9. The coupler of example 7 or 8, wherein the L shapes are positioned symmetrically about the section of the metal layer so as to form mirror images of each other with respect to the section of the metal layer.

10. The coupler of one or any combination of the previous examples, further comprising two of the waveguides embedded in the metal layer, wherein each waveguide is a mirror image of the other waveguide about an axis of symmetry of the metal layer.

11. The coupler of example 10, wherein the openings each have an L shape having a base portion and a back portion; the L shapes in each waveguide are positioned symmetrically about the section of the metal layer so as to form mirror images of each other with respect to the section of the metal layer, and a perpendicular distance between the base portions, in one of the waveguides, to the base portions in the other waveguide in the pair, is in a range of $\lambda/2$-$3\lambda$ or 2-10 mm in the demonstration.

12. The coupler of example 11, wherein the reflective surface is rectangular and has sides having a length in a range of $3\lambda$-$15\lambda$, or 10-50 mm in this demonstration.

13. The coupler of example 11, wherein the reflective surface is rectangular and has a first side opposite a second side, the first side and the second side each having a length in a range of $3\lambda$-$15\lambda$, or 10-50 mm in this demonstration; the waveguides include a first waveguide and a second waveguide, the openings and the section in the first waveguide extend to the first side, and the openings and the section in the second waveguide extend to the second side.

14. The coupler of one or any combination of the previous examples, wherein the waveguides each comprise a stripline including the section of metal between two sections of the ground plane.

15. The coupler of one or any combination of the previous examples, wherein the coupler is coupled to a second mirror so as to form a cavity confining the electromagnetic radiation and generating modes of the electromagnetic radiation in the cavity when the electromagnetic radiation is coupled into the cavity through the one or more waveguides coupler. The modes comprise peaks and troughs of a cavity electric field evenly spaced along the cavity's longitudinal axis, and the cavity electric field is symmetrically distributed in at least one direction perpendicular to the cavity axis.

16. The coupler of example 15, wherein the cavity electric field at a first point and a second point symmetrically positioned on either side of the cavity's axis are the same to within 10%.

17. The coupler of example 16, wherein the first point and the second point are each at a same distance in a range of λ-3λ, 3-10 mm in this demonstration, from the axis.

The coupler is comprised of a slot (the short legs of the "Ls") that radiates the signal into the semi-confocal resonator. It radiates due to an electric field across the slot that is excited by a short "stub" antenna that receives the signal from the transmitter along a coplanar waveguide (CPW) transmission line (the two parallel long legs of the "L"s). The cluster of via holes confines the signal to the CPW line and the slot, preventing it from leaking into the dielectric region under the top ground plane. The second slot works in reverse to convey the resonator signals to the receiver.

The coupler radiates only weakly into the resonator, requiring several hundred cycles of the signal to build up the electric field in the resonator to its peak value. This is required to enable the resonator to have the high quality factor necessary for operation: the reciprocity principle of electromagnetism dictates that a more efficient radiator would also allow the signal to leak prematurely back into the CPW lines to the transmitter and receiver.

The present disclosure further describes a spectrometer including the coupler of one or any combination of the examples described above. The spectrometer includes a transmitter coupled to the coupler, wherein the transmitter transmits an electric field to the coupler and the electric field is transmitted along the waveguide and generates the electromagnetic radiation outputted from the coupler into the cavity. The spectrometer further includes a receiver coupled to the coupler for receiving an output electric field transmitted along the waveguide in response to a presence of a molecule in the cavity interacting with the cavity electrical field of the electromagnetic radiation. A computer coupled to the receiver determines a composition of the molecule from the output electric field.

In one or more examples, the transmitter includes a first output electrically connected to the center section of the waveguide at a side of the metal layer; and a second output electrically connected to the ground plane at the side of the metal layer so as to apply an electrical field across the section and the ground plane. The spectrometer further includes a receiver including a first input electrically connected to the section of the waveguide at the side of the metal layer, and a second input electrically connected to the ground plane so as to receive the output electrical field applied across the section of the waveguide and the ground plane in response to the molecule in the cavity interacting with the cavity electrical field.

BRIEF DESCRIPTION OF THE DRAWINGS

Referring now to the drawings in which like reference numbers represent corresponding parts throughout:

FIG. 1A illustrates a coupler according to one embodiment of the present invention.

FIG. 1B illustrates a waveguide embedded in the coupler, according to one or more embodiments of the present invention.

FIG. 1C and FIG. 1D illustrate couplers with different waveguide lengths, according to one or more embodiments, wherein FIG. 1C illustrates a coupler with a waveguide having a 2λ, 7 mm in this example, length (coupler A) and FIG. 1D illustrates a coupler with a 1.5λ, 5 mm in this example, length (Coupler B). The waveguides in FIGS. 1C and 1D are both terminated with ¾ λ, 2.5 mm in this example, wide edges.

FIGS. 4A-4D. The S-parameters obtained from VNA measurements are plotted for all of W-band (FIG. 4A, 4B) and expanded for the SpecChip bandwidth (FIG. 4C, 4D). The data for Coupler A (FIG. 1C) is shown in FIGS. 4A, 4C; the data for Coupler B (FIG. 1D) is shown in FIGS. 4B and 4D. Reflections off the input (S11) and output (S22) are typically 80%, but periodic drops to as low as 20% are observed. When both the transmitter and receiver have low reflections at the same wavelengths (FIG. 4A, 4C), transmission (S12/S21) is boosted; however, the cavity is less isolated, causing the finesse (and Q-factor) to drop.

FIG. 5C illustrates a transmitter (TX) attached to the coupler, according to one or more embodiments. The receiver (not shown) is attached in analogous fashion.

DETAILED DESCRIPTION OF THE INVENTION

Figure 2:
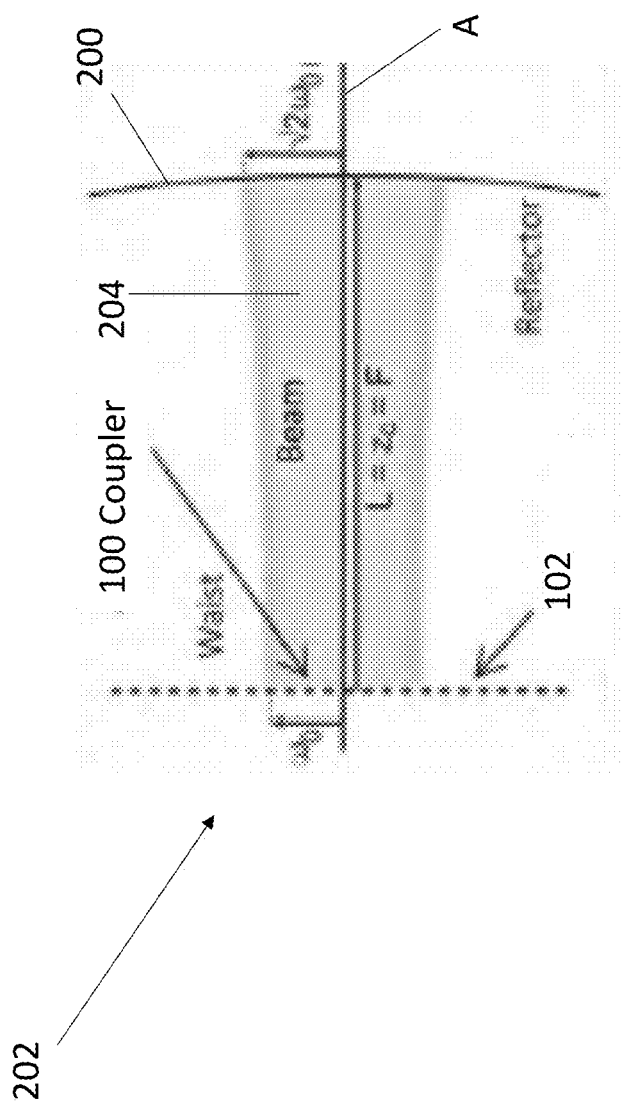
FIG. 2 illustrates a cavity including the coupler, according to one or more embodiments.

In the following description of the preferred embodiment, reference is made to the accompanying drawings which form a part hereof, and in which is shown by way of illustration a specific embodiment in which the invention may be practiced. It is to be understood that other embodiments may be utilized and structural changes may be made without departing from the scope of the present invention.

Technical Description

Coupler Example

FIG. 1A illustrates a coupler 100 for electromagnetic radiation, comprising a metallic (e.g. gold, copper) mirror or reflector 102, that constitutes or comprises also the grounded co-planar waveguide elements; i.e. one or more waveguides 110 for gigahertz or terahertz electromagnetic radiation embedded in a metal layer 104 that includes a ground plane 108 and has a reflective surface 106. The metal layer 104 is deposited on a substrate (e.g., a dielectric 112 such as Duroid). Examples of electromagnetic radiation include, but are not limited to, electromagnetic radiation having a wavelength, $\lambda$ (e.g., at band center), between 0.5-5 mm. Examples of electromagnetic radiation include, but are not limited to, electromagnetic radiation having a frequency between 0.06 and 0.6 Terahertz, or 60-600 Gigahertz. The coupler 100 further includes the main ground plane (not shown) under the substrate.

FIG. 1B further illustrates each of the waveguides 110 include two openings 114 or slots in the metal layer exposing a dielectric 112 underneath; and a (e.g., rectangular) section 116 (e.g., strip) of the metal layer between the two openings. Example dimensions for the openings include, but are not limited to, a width W1 in a range of $\lambda/5$-$\lambda/2$, 600-1500 micrometers in this example, and a length L1 in a range of $1.5\lambda$-$15\lambda$, 5-15 mm in this example. Example dimensions for the strip 116 include, but are not limited to, a width W2 in a range of $\lambda/5$-$\lambda/2$ or 600-1500 micrometers and a length L2 in a range of $3\lambda$-$15\lambda$ or 5-15 mm. In the example of FIGS. 1A-1B, the waveguide 110 is a stripline including the section of metal between two sections of the ground plane 108.

FIG. 1B further illustrates a plurality of holes 118 are disposed in the metal layer along an edge of the openings. The holes expose the dielectric under the metal layer. In one or more examples, the holes are disposed around a perimeter of the waveguide. In one or more further examples, the holes are disposed in pattern including, but not limited to, a hexagonal pattern 120 or rows 122 (e.g., 2-4 rows). Example dimensions for the holes include, but are not limited to, a diameter D or a width in a range of $\lambda/15$-$\lambda/5$ or 200-600 micrometers. Example hole spacings include, but are not limited to, a spacing in a range of $\lambda/5$-$\lambda/2$ or 600-1500 micrometers (distance from a center of one hole to a center of an adjacent hole) and are dependent on the chosen substrate which is not necessary the Duroid depicted in the example.

In the example illustrated in FIGS. 1A and 1B, the openings 114 each have an L shape having a base portion 124 and a back portion 126 wherein the L shapes are positioned symmetrically about the section of the metal layer so as to form mirror images of each other with respect to the section of the metal layer. Example dimensions of the base portion are such that a length L3 (the sum of the lengths of two base portions 124 and the strip width W2) is a range of $\lambda/2$-$4\lambda$, or 1-4 mm. Example dimensions of the back portion include, but are not limited to, a length L1, L2 in a range of $3\lambda$-$15\lambda$, or 5-15 mm.

In the examples illustrated in FIG. 1C and FIG. 1D, the coupler 100 includes two (a pair of) waveguides 110a, 110b embedded in the metal layer 104 so that each waveguide 110a, 110b is a mirror image of the other waveguide about an axis of symmetry 128 of the metal layer. FIG. 1C illustrates a coupler with a waveguide having a length L2=7 mm (coupler A) and FIG. 1D illustrates a coupler with a length L2=5 mm length (Coupler B). The waveguides in FIGS. 1C and 1D are both terminated with L3=2.5 mm wide edges. In one or more examples, a perpendicular distance 130 between the base portions 124, in one of the waveguides 110a in the pair, to the base portions in the other waveguide 110b in the pair, is in a range of $\lambda/2$-$3\lambda$ or 2-10 mm in this demonstration.

FIG. 1C and FIG. 1D further illustrate an example wherein the reflective surface 102 is rectangular (square) and has sides 132a, 132b having a length 134 in a range of $\lambda$-$15\lambda$, or 10-50 mm in this demonstration. The openings 114 and the section 116 in the first waveguide 110a extend to the first side 132a, and the openings 114 and the section 116 in the second waveguide 110b extend to the second side 132b opposite the first side 132a.

Example Coupler Design for Use in a Cavity

The development of an efficient coupler plate was achieved by running full electromagnetic field simulations on a series of test designs using the high-frequency simulation software (HFSS) package by ANSYS. This analysis tool allows for the visualization of cavity mode structures as well as graphical display of transmitted power and phase rotation. Due to the computationally intensive calculations required for fully modeling the coupler plate waveform in three dimensions, the mode structures were calculated with a concave mirror at a closer distance (10 mm) than those used (25 mm or 50 mm) for the experimental demonstration examples described herein.

FIG. 2 illustrates the coupler 100 coupled to a second mirror 200 so as to form a cavity 202 confining electromagnetic radiation 204. The mode structures (from TEMnm, n,m=0, 1, 2, . . . ) were found to be strongly dependent on (1) the distance 130 between the coupler feeds (waveguides 110), which extend from the edges of the planar mirror 102 where the chips (transmitter 302 and receiver 304) are mounted, to a central, completely reflective region; (2) the positioning of via holes 118 that shape the beam 204 as it exits or enters the plane; (3) the distance to and diameter of the spherical mirror 200, which allows preferential discrimination against higher order modes (n,m>0).

Figures 3A, 3B:
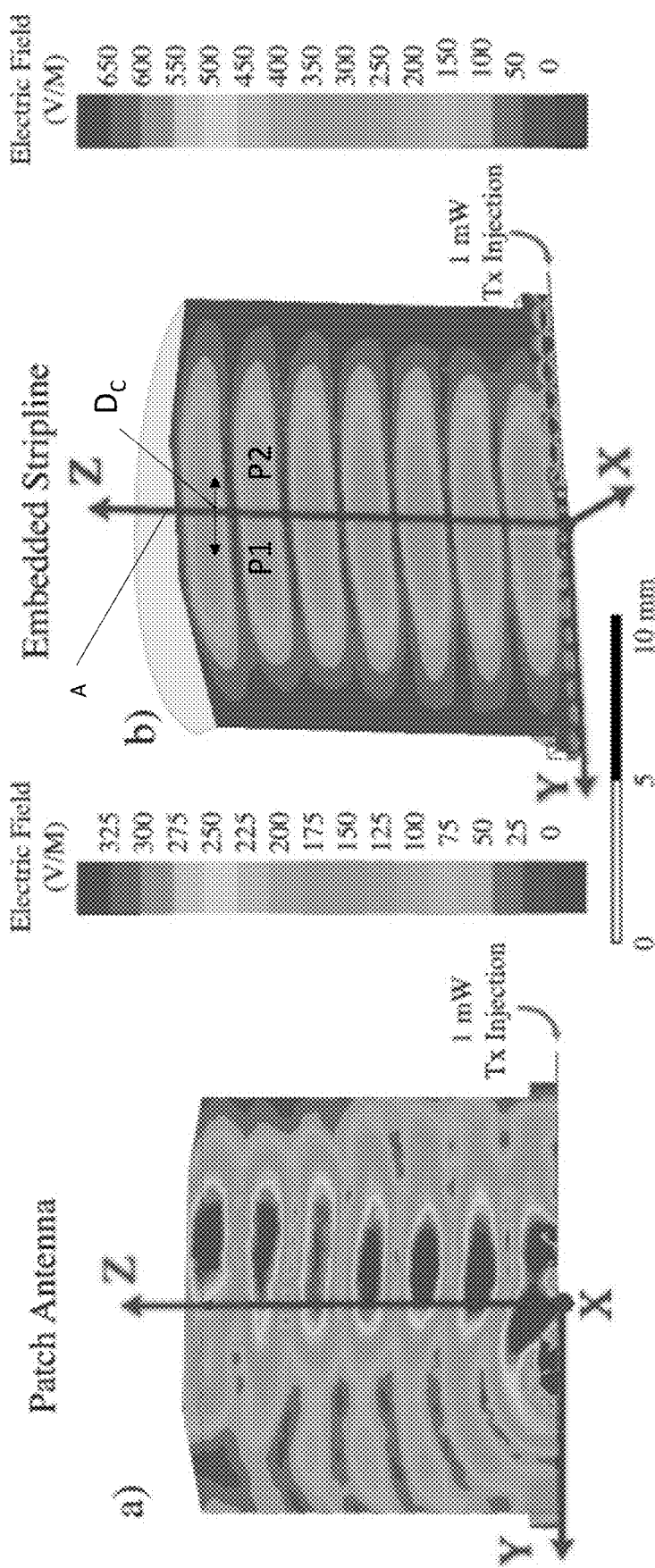
FIGS. 3A-3B. Two dimensional slice of simulated results highlighting drastically different coupler emission properties for patch antenna (FIG. 3A) and embedded coplanar waveguide (FIG. 3B) test designs. In both examples, 1 mW of continuous wave radiation is injected into the right side of the coupler plate, which is positioned in the XY plane. An optical cavity is established with a concave reflector (not depicted) that is positioned 10 mm away from the coupler normal to the Z-axis.
Figures 4C, 4D:
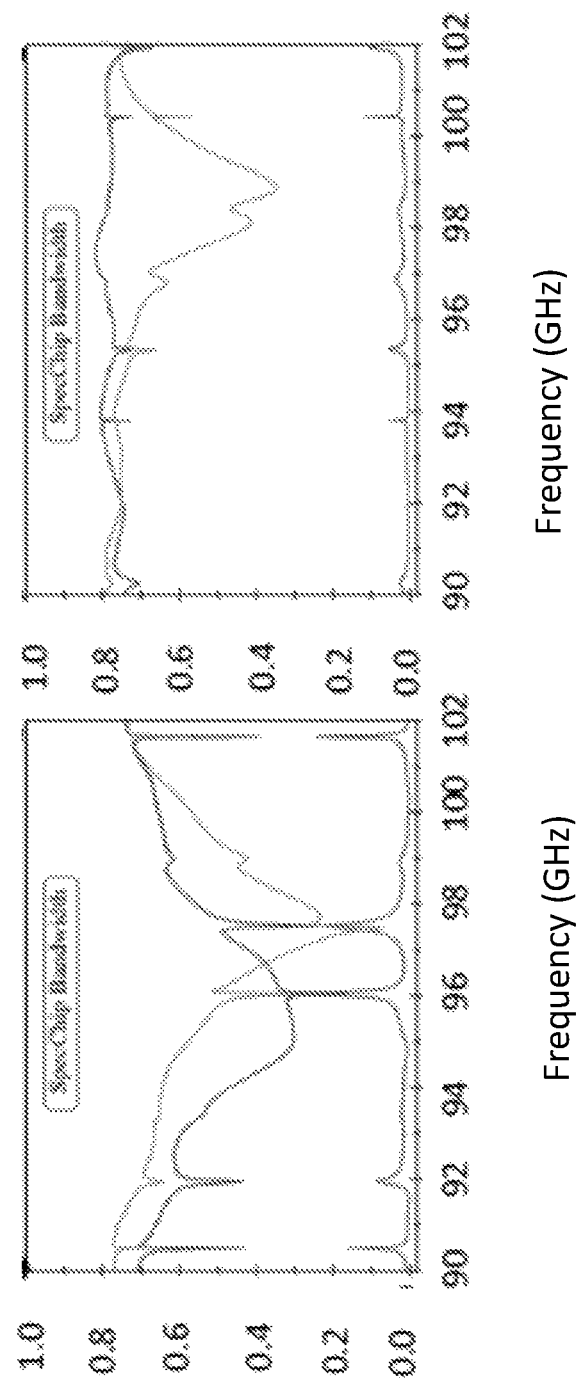

Initial attempts using traditional patch antenna designs, where an example simulation is depicted in FIG. 3A, produced unsatisfactory results with mode structures found to be off-axis with respect to the optical cavity and responses found to vary dramatically across the instrument bandwidth. The coupler illustrated in FIGS. 1A, 1B, 1C, and 1D, on the other hand, including carefully positioned "via" holes 118 paired with coplanar waveguides 110 to which the transmitter can be wire bonded directly, was found to provide a balanced response independent of the injected radiation wavelength, see FIG. 3B. Specifically, FIG. 3B illustrates the coupler coupled to a second mirror forms a cavity confining the electromagnetic radiation and generating modes of the electromagnetic radiation in the cavity when the electromagnetic radiation is coupled into the cavity through the one or more waveguides. The modes comprise strong field regions (peaks) that can interact with a molecule, and troughs/nodes of a cavity electric field, wherein the peaks and nodes are evenly spaced along the cavity's longitudinal axis A. Moreover, the cavity electric field is symmetrically distributed in at least one direction perpendicular to the cavity axis. In one or more examples, symmetry of the cavity electric field is characterized by the cavity electric field at a first point P1 and a second point P2 symmetrically positioned on either side of the cavity's axis A being the same to within 10% (e.g., when the first point P1 and the second point P2 are each at a same distance in a range of λ-3λ, or 3-10 mm in this demonstration, from the axis). The holes are disposed around the perimeter of the waveguide so as to inject the radiation deep into the central portion of the coupler (achieving some isolation) and to establish the symmetrical distribution of the cavity electric field.

Copper-plated Duroid coupler structures achieving the field profile of FIG. 3(b) were fabricated (as shown in FIGS. 1C and 1D) and tested. To test the performance properties of the fabricated coupler designs, freestanding units were constructed consisting of a coupler plate mounted onto an aluminum base with wire probes used to connect the embedded coplanar waveguides to standard WR10 waveguide flanges for interfacing with standard mm-wave laboratory equipment. An optical cavity, as illustrated in FIG. 2, was established/aligned with a kinematic mounted concave mirror and translation stage. Measurements with a W-band vector network analyzer (VNA) (instead of a CMOS Tx/Rx integrated circuit), time gated to remove the influence of waveguide coupling, were performed to provide insight into the input ($S_{11}$) and output ($S_{22}$) reflection properties as well as total transmission ($S_{12}/S_{21}$) of the isolated coupler. A subset of these measurements is plotted in FIGS. 4A-4D which show that the input and output reflections are largely symmetric, although having a frequency shift hinting at fabrication asymmetries.

A molecule having electromagnetic transition defined by energy levels separated by an energy E=hv can interact with electromagnetic radiation having a frequency v. In a cavity, energy of the electromagnetic radiation can be resonantly transferred into the molecule. The resonant transfer results in transient absorption and subsequent emission that is characteristic to the molecule. The efficiency and lifetime of the resonant transfer of energy is in part determined by the linewidth of the cavity modes (transmission peaks 400) illustrated in FIG. 4A-4B (larger linewidths indicating shorter lifetime of the cavity electric field in the cavity and therefore weaker coupling to molecular electromagnetic transitions shorter lifetimes/reduced efficiency for the resonant transfer). FIG. 4A and FIG. 4B illustrate linewidths that are (surprisingly and unexpectedly) 10 times narrower than predicted by simulations, indicating that the coupler enables significantly stronger interaction between the molecule and the electromagnetic radiation. As a result, molecular compositions can be extracted from cavity absorption spectra with accuracy and efficiency.

FIGS. 4A-4D further illustrates that the length L2 of the waveguides 110 can be tuned to control the amount of electromagnetic radiation energy inputted into the cavity 202. Coupler A (FIG. 1C) having the shorter waveguide length L2 (as compared to coupler B shown n FIG. 1D) coupled a larger amount of electromagnetic radiation that was confined in the cavity for a longer period of time (as evidenced by the taller resonance peaks 400 in FIG. 4A as compared to FIG. 4B).

In one or more examples it is desirable to maximize the amount of energy inputted into the molecules interacting with the cavity electric field. However, there is a quantum limit to the amount of energy that can be inputted into the molecules (excess amounts of energy inputted into the cavity beyond the quantum limit are not resonantly transferred between the molecule and the cavity electric field; instead, the excess energy induces a coherent, non-emissive state that reduces sensitivity. As illustrated herein, the amount of energy coupled to the molecules can be tailored depending on the molecule and cavity by tuning the coupler (e.g., tuning lengths L2/L3 of the waveguides 110). In one or more embodiments, the lengths L2 and/or L3 of the waveguides 110, as well as the timing controls of the injected radiation, are tailored so that an amount of energy transferred to a molecule in the cavity 202 from the electromagnetic radiation 204 inputted into the cavity 202, does not exceed a quantum limit. In one or more embodiments, the lengths L2 and L3 are tailored so that cavity's modewidth is wider than the targeted absorption feature of the molecule being analyzed.

Figure 8:
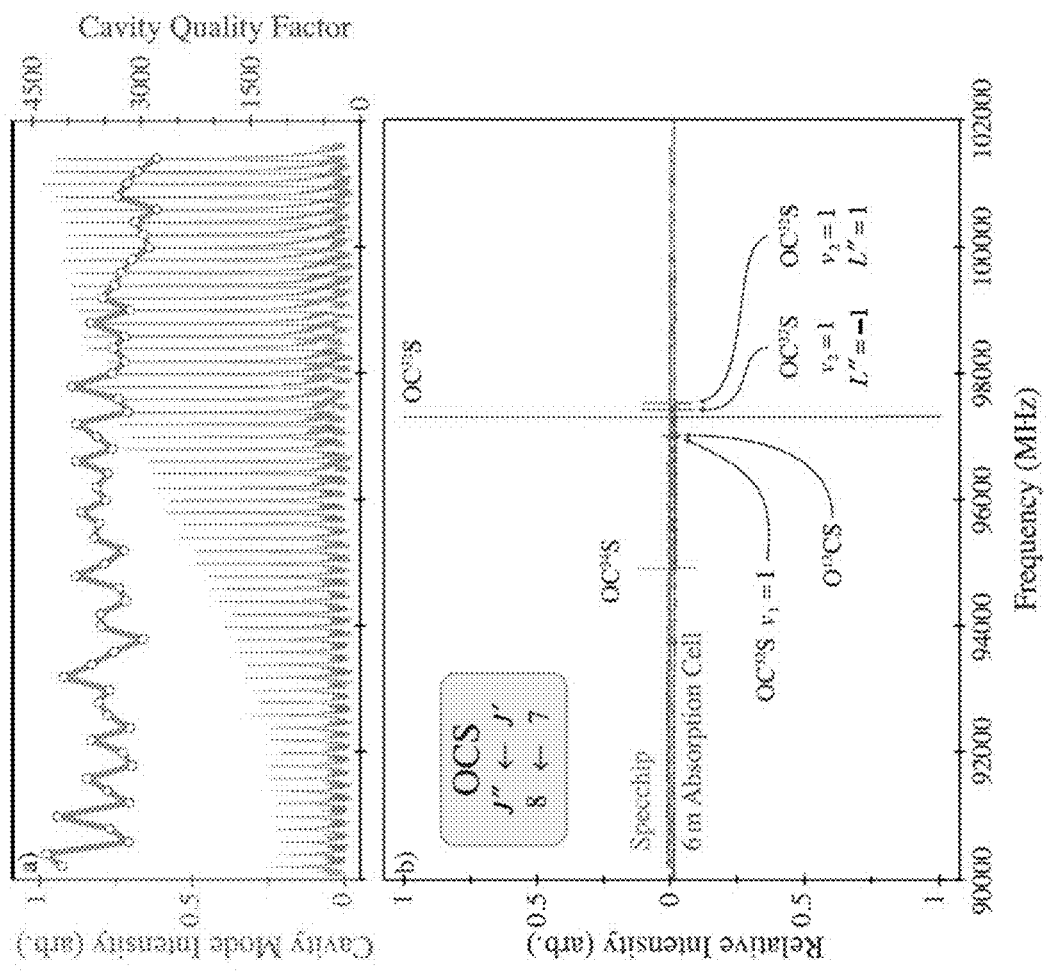
FIG. 8. Evolution of a single cavity mode (a) tracked across the bandwidth of the SpecChip instrument outfitted with a 50 mm focal length, f=50 mm, 50 mm diameter, φ=50 mm end mirror, 50 mm corresponds to 15λ at band center. Each mode was fit with a Lorentzian line shape to extract cavity quality factors which are also plotted. The bottom panel depicts bulk, 3 mTorr, OCS survey scans taken with the pulsed SpecChip instrument (green) and with a traditional frequency-modulated absorption spectrometer (purple).

The Q-factors extracted from the transmission trace ranged from 1000 to 4000 across all of W-band, a finding which is in alignment with the results observed in the spectrometer system (cf., FIG. 8) over its narrower functioning bandwidth. After VNA testing, couplers having the desired balance between cavity quality factors, injection power, and isolation were selected for circuit board integration.

Example Spectrometer for Measuring the Composition of a Molecule

In this example, the coupler mounted with waveguide access was used to create a pulsed Fourier-transform millimeter-wave spectrometer. Additional uses of this coupler may include, but are not limited to, a tunable THz radiation filter or a passive amplifier for free-space coupling.

Figure 5B:
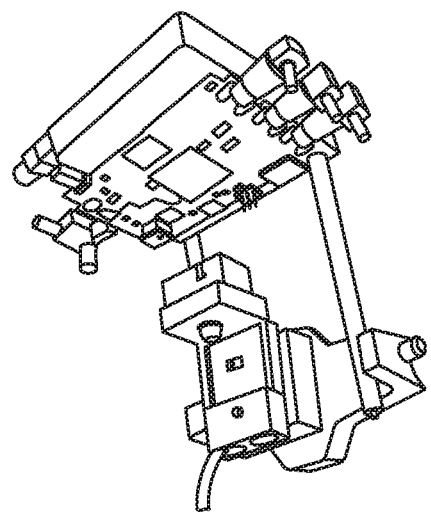
FIG. 5B illustrates the spectrometer including the coupler and a translation stage, according to one or more embodiments.
Figure 5A:
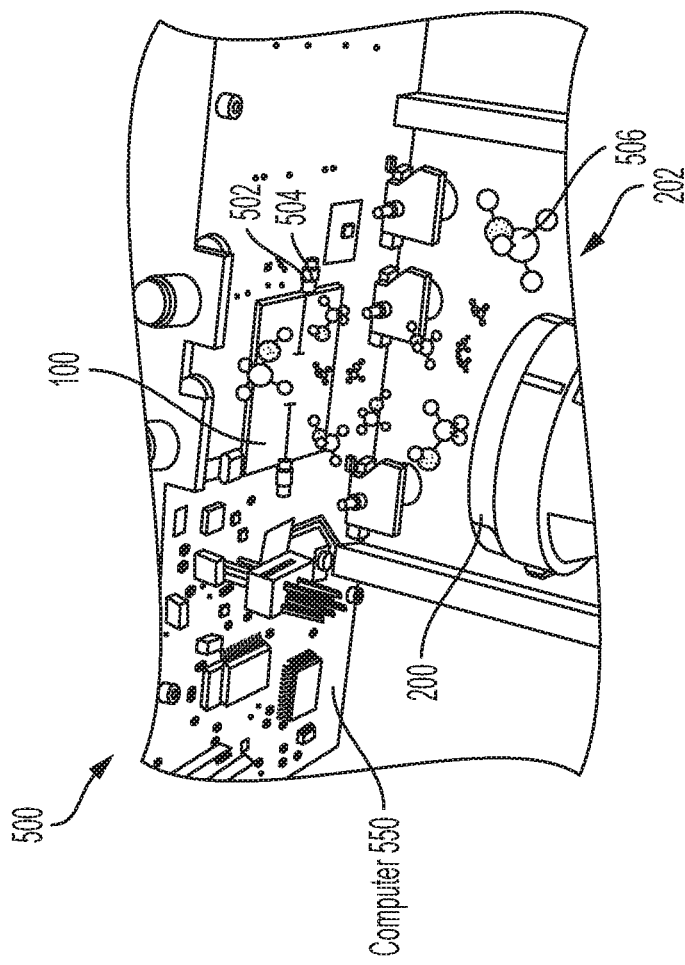
FIG. 5A illustrates a spectrometer including the coupler according to one or more embodiments.

FIGS. 5A-5B illustrate a spectrometer 500 including the coupler 100, the cavity 202, and a transmitter 502 and receiver 504 coupled to the coupler. The transmitter transmits an input electric field to the coupler and the input electric field is transmitted along the waveguide 110 so as to generate the electromagnetic radiation 204 outputted from the coupler into the cavity 202. In one or more examples, the input electric field is inputted at a first end 150 of the waveguide 110 and the input electric field transmitted along the waveguide generates the electromagnetic radiation 204 radiating from a second end 152 of the waveguide at the base portion 124. The electromagnetic radiation 204 is confined in the cavity by reflecting between the reflective surface 106 of the metal layer 104, including at central region 160 of the reflective surface 106 between the waveguides 110, and the second mirror 200.

The receiver 504 coupled to the coupler 100 receives an output electric field transmitted along the waveguide in response to a presence of a molecule 506 in the cavity interacting with the cavity electrical field of the electromagnetic radiation 204. A computer 550 coupled to the receiver 504 determines a composition of the molecule from the output electric field.

FIG. 5B illustrates an example wherein, to create a high-finesse cavity mode structure with the coupler circuit, a round, gold-plated, spherical mirror with 2.5 cm focal length is mounted on a precision translation stage (PI MikroMove stage providing submicron translations) approximately three cm above the coupler and fixed along the perpendicular axis projected from the coupler's central area.

FIG. 5C illustrates the transmitter 502 includes a first output 507 electrically connected (e.g., via wire 508) to the section/strip 116 at the side 132a of the metal layer; and a second output 510 electrically connected (e.g. via wire 512) to the ground plane 108 at the side 132a. The first output 507 and second output 510 apply the input electrical field between the section/strip 116 and the ground plane 108. The receiver 504 includes a first input 514 electrically connected (e.g., via wire 508) to the section/strip 116 at the side 132a and a second input 516 electrically connected (e.g. via wire 512) to the ground plane 108. The first input 514 and the second input 516 receive the output electrical field applied between the section/strip 116 and the ground plane 108 in response to the molecule 506 in the cavity 202 interacting with the cavity electrical field.

In one or more examples, the spectrometer system includes PCB-mounted source and detection electronics including a chip-based RF synthesizer (SiLab 5340b, 3 W) and the two custom CMOS chips (0.3 W). In one or more examples, the chips (transmitter and receiver) and coupler are embedded on a custom printed circuit board along with an Atmega processor and universal serial bus interface. A command/control program developed for operations of both the Tx and Rx chips can be loaded onto the processor and simple commands can be used to adjust pulse lengths, amplifier gains, or dispatch several algorithms used to automatically lock the synthesizers. In one or more examples, both Tx and Rx chips have embedded synthesizers tunable in the 92-104 GHz range, these initial checkouts utilize an external source generator that is more finely tunable (<1 kHz tuning possible at 92-104 GHz). Combined with the space requirements of the piezo-mounted end mirror, the device illustrated in FIG. 5B occupies only ~1 liter of total volume.

Figure 6:
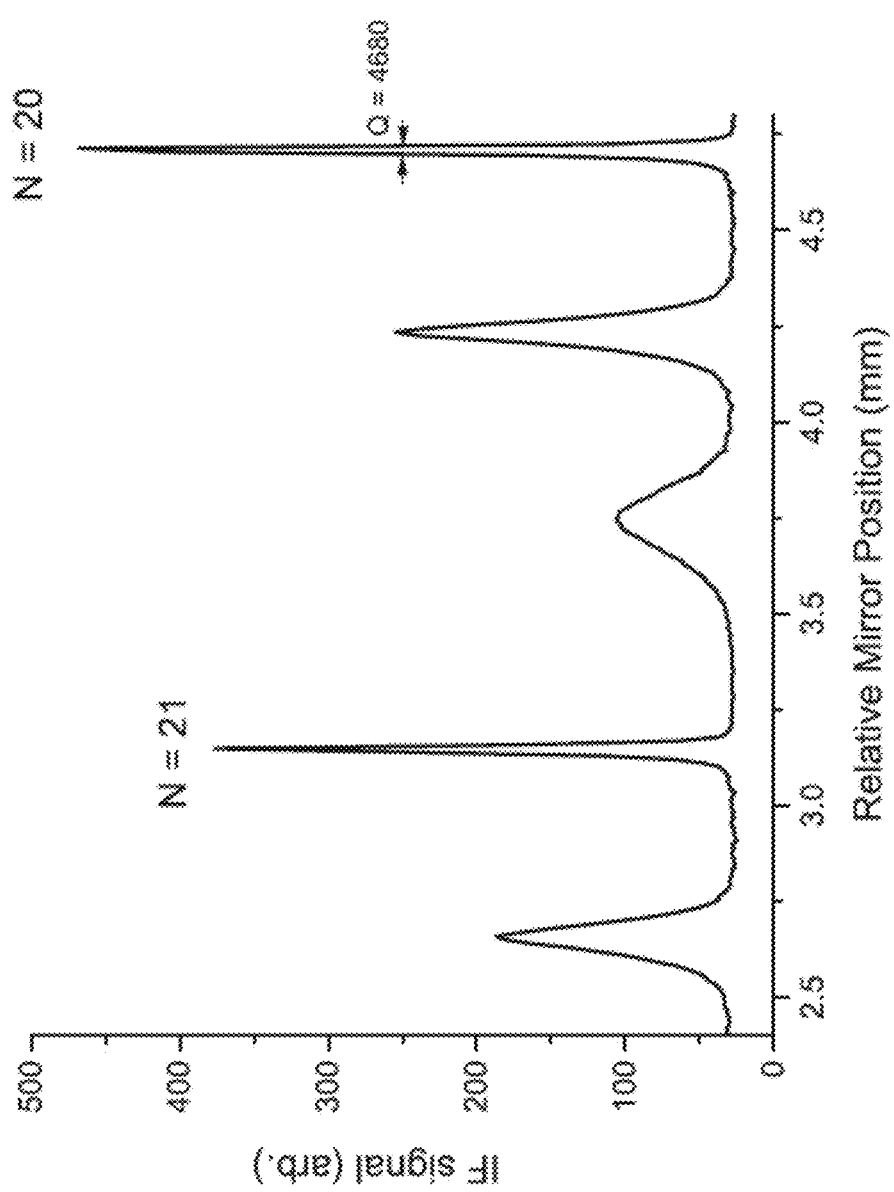
FIG. 6 illustrates results of a Mirror position scan over 2 mm (λ/2 at 100.5 GHz is 1.49 mm) displaying primary (TEM00 with sharp narrow features), secondary (TEM01 intermediate features), and a tertiary TEM02 mode.

For the measurements described herein, the reflexive coupler was designed onto the surface of a gold-plated circuit board that can also act as a flat mirror in a semi-confocal Fabry-Perot (FP) cavity, as illustrated in FIG. 5A and FIG. 5B. Results of mirror position scans reveal cavity mode structures and positions (see FIG. 6) for a given transmission (Tx) frequency. Alignment of the circuit board normal to the positioner axis dramatically improves the symmetry and quality factors of observable modes. The higher order modes, which have a wider spatial footprint as they radiate off the coupler, are observed to decrease in magnitude more rapidly than the primary (nodeless) TEM00 mode, which has the highest quality factor for a given mode number. The mode number is the number of wavelengths spanning the round-trip cavity distance for a given mirror position. The decrease in quality factor with mode order (TEMnm, n,m>0) is an indicator of the domination of diffractive losses in this system. Tests with larger diameter mirrors indicate a significant increase in the mode structure that can lead to interferences at specific frequencies. Positioning of the stage with respect to detected modes is highly reproducible and modes are easily tracked in frequency space with mirror position adjustments.

Figure 7:
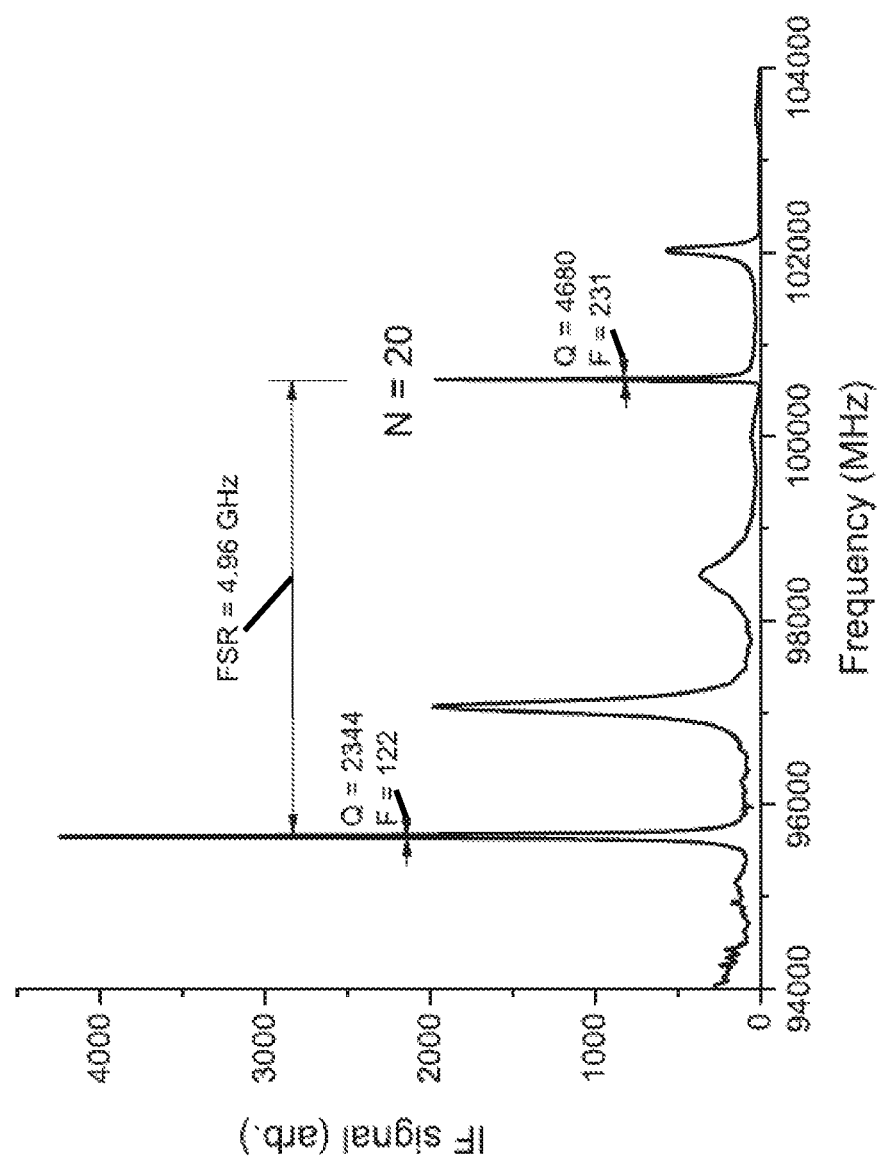
FIG. 7 illustrates a frequency scan over 10 GHz displaying primary (TEM00 with sharp narrow features), secondary TEM01 (intermediate features) and a broad tertiary TEM02 mode. The free spectral range is 4.96 GHz and the primary modes have quality factors (Q) of 2344 and 4680 and finesses (F) of 122 and 231 at lower and higher frequencies, respectively.

A suitable driving signal for Tx and Rx is chosen, usually with a fixed intermediate frequency (IF) and the two may then be scanned to determine the frequency response of the system. For small scans (<100 MHz, or within a primary mode) the oscillators inside the chips remain locked over the scan range. In one or more examples, scanning across the full bandwidth (see FIG. 7) is achieved by periodic re-locking of the oscillators through the command interface. The same primary, secondary, and tertiary mode structures are observed in frequency and position scanning. The modes shift under vacuum conditions due primarily to the change in refractive index of the medium.

Figure 9:
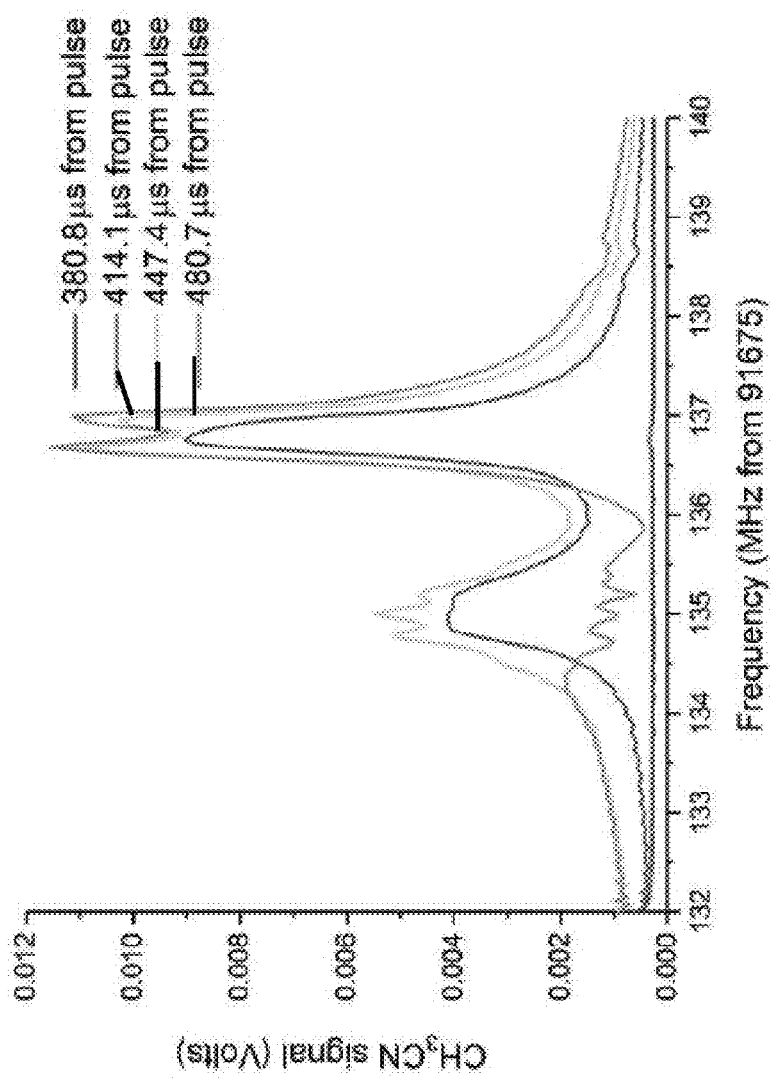
FIG. 9 spectrum obtained using the spectrometer including the coupler, according to one or more examples.

FIG. 9 illustrates a signal obtained using the spectrometer including the coupler when the cavity contains $CH_3CN$ molecules interacting with the electromagnetic radiation inputted into the cavity through the waveguide 110 in the coupler 100. The signal is derived from the output electric field received in the receiver from the waveguide 110 in the coupler 100.

Process Steps

Figure 10:
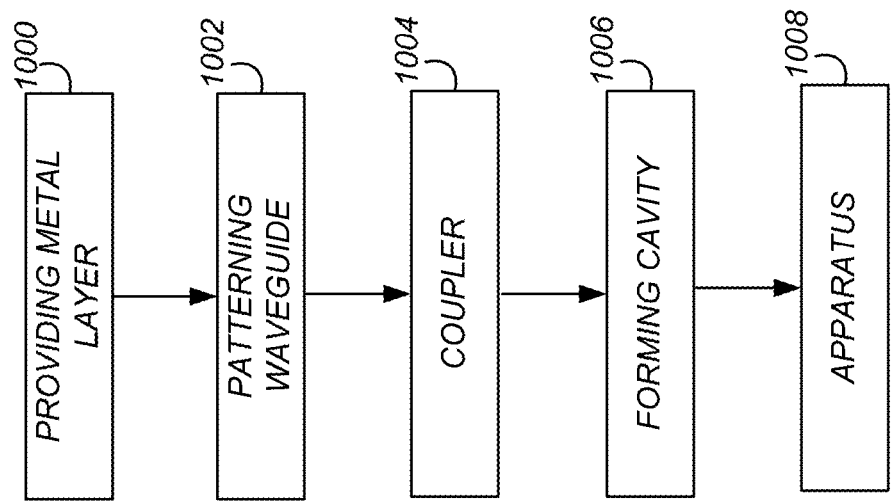
FIG. 10 is a flowchart illustrating a method of making a coupler, according to one or more examples.

FIG. 10 is a flowchart illustrating a method of making a coupler for coupling electromagnetic radiation having a wavelength λ (e.g., at band center) into a cavity, according to one or more embodiments (referring also to FIGS. 1A-1D, 2, 4, and 5A-5C.

Block 1000 represents providing a mirror 102 including a metal layer 104 having a reflective surface 106 on a substrate. The metal layer 104 includes a ground plane 108. A main ground plane is formed on a backside of the substrate.

Block 1002 represents patterning one or more waveguides 110 for gigahertz or terahertz electromagnetic radiation so that each of the waveguides are embedded in the metal layer 104 and include (1) two openings 114 in the metal layer 104 exposing a dielectric 112 under the metal layer 104; and (2) a section 116 of the metal layer 104 between the two openings. The patterning further comprises patterning a plurality of holes 118 in the metal layer 104 disposed along an edge of the openings 114, the holes exposing the dielectric under the metal layer.

Block 1004 represents the end result, a coupler 100. The coupler can be embodied in many ways including, but not limited to the following.

1. The coupler wherein the holes 118 are disposed around a perimeter of the waveguide 110.

2. The coupler wherein the holes 118 are disposed in a hexagonal pattern.

3. The coupler of one or any combination of the previous examples wherein the holes have a diameter D or a width in a range of λ/15-λ/5 or 200-600 micrometers.

4. The coupler of one or any combination of the previous examples wherein the holes 118 are separated by a distance in a range of λ/5-λ/2 or 600-1500 micrometers (distance from a center of one hole to a center of an adjacent hole)

5. The coupler of one or any combination of the previous examples wherein the holes 118 are disposed in 2-4 rows.

6. The coupler of one or any combination of the previous examples, wherein the openings 114 in the waveguide 110 have a width W1 in a range of λ/5-λ/2, where λ is the wavelength at band center, or 600-1500 micrometers.

7. The coupler of one or any combination of the previous examples, wherein the openings each have an L shape having a base portion 124 and a back portion 126.

8. The coupler of example 7, wherein the base portion 124 has a length L5 in a range of λ/2-4λ, or 1-4 mm and the back portion 126 has a length L1 in a range of 3λ-15λ, or 5-15 mm.

9. The coupler of example 7 or 8, wherein the L shapes are positioned symmetrically about the section 116 of the metal layer 104 so as to form mirror images of each other with respect to the section 116 of the metal layer 104.

10. The coupler of one or any combination of the previous examples, further comprising two of the waveguides 110 embedded in the metal layer 104, wherein each waveguide 110a is a mirror image of the other waveguide 110b about an axis of symmetry 128 of the metal layer 104.

11. The coupler of example 10, wherein the openings 114 each have an L shape having a base portion 124 and a back portion 126; the L shapes in each waveguide 110a, 110b are positioned symmetrically about the section 116 of the metal layer 104 so as to form mirror images of each other with respect to the section of the metal layer 104, and a perpendicular distance 130 between the base portions 124, in one of the waveguides 110a, to the base portions 124 in the other waveguide 110b in the pair, is in a range of $\lambda/2$-$3\lambda$ or 2-10 mm.

12. The coupler of example 11, wherein the reflective surface is rectangular and has sides having a length 134 in a range of $3\lambda$-$15\lambda$, or 10-50 mm.

13. The coupler of example 11, wherein the reflective surface is rectangular and has a first side opposite a second side, the first side and the second side each having a length in a range of $3\lambda$-$15\lambda$, or 10-50 mm; the waveguides include a first waveguide and a second waveguide, the openings and the section in the first waveguide extend to the first side, and the openings and the section in the second waveguide extend to the second side.

14. The coupler of one or any combination of the previous examples, wherein the waveguides 110 each comprise a stripline including the section of metal between two sections of the ground plane 108.

Block 1006 represents optionally coupling the coupler 100 to a second mirror 200 so as to form a cavity 202 confining the electromagnetic radiation and generating modes of the electromagnetic radiation in the cavity when the electromagnetic radiation is coupled into the cavity through the coupler. The modes comprise peaks 400 and nodes of a cavity electric field evenly spaced along the cavity's longitudinal axis (cavity axis), and the cavity electric field is symmetrically distributed in at least one direction perpendicular to the cavity axis. In one example, the cavity electric field at a first point P1 and a second point P2 symmetrically positioned on either side of the cavity's axis are the same to within 10%. In one or more further examples, the first point and the second point are each at a same distance in a range of $\lambda$-$3\lambda$ or 3-10 mm, from the axis.

The coupler 100 is comprised of a slot 124, 124a (the short legs of the "Ls") that radiates the signal (e.g., as electromagnetic radiation 204 into the semi-confocal resonator 202. The slot 126a radiates due to an electric field across the slot that is excited by a short "stub" antenna that receives the signal from the transmitter 502 along a coplanar waveguide (CPW) transmission line (the two parallel long legs 126a, 126 of the "L"s). The cluster of via holes 118 confines the signal to the CPW line and the slot, preventing it from leaking into the dielectric 112 region under the top ground plane 108. The second slot 124b works in reverse to convey the resonator signals to the receiver 504.

The coupler 100 radiates only weakly into the resonator 202, requiring several hundred cycles of the signal to build up the electric field in the resonator to its peak value. This is required to enable the resonator to have the high quality factor necessary for operation: the reciprocity principle of electromagnetism dictates that a more efficient radiator would also allow the signal to leak prematurely back into the CPW lines to the transmitter and receiver.

Block 1008 represents providing an apparatus (e.g., spectrometer 500, amplifier, or filter) including the coupler of one or any combination of the examples described above. The spectrometer/apparatus includes a transmitter 502 coupled to the coupler 100, wherein the transmitter transmits an electric field to the coupler and the electric field is transmitted along the waveguide and generates the electromagnetic radiation outputted from the coupler into the cavity. The spectrometer/apparatus further includes a receiver 504 coupled to the coupler for receiving an output electric field transmitted along the waveguide in response to a presence of a molecule in the cavity interacting with the cavity electrical field of the electromagnetic radiation. A computer coupled to the receiver determines a composition of the molecule from the output electric field.

In one or more examples, the transmitter includes a first output electrically connected to the center section of the waveguide at a side of the metal layer; and a second output electrically connected to the ground plane at the side of the metal layer so as to apply an electrical field across the section and the ground plane. The spectrometer further includes a receiver including a first input electrically connected to the section of the waveguide at the side of the metal layer, and a second input electrically connected to the ground plane so as to receive the output electrical field applied across the section of the waveguide and the ground plane in response to the molecule in the cavity interacting with the cavity electrical field.

Advantages and Improvements

Previous attempts to utilize mm-wave cavities for pulsed detection schemes have largely been stymied due to difficulties with coupling radiation efficiently into high finesse cavities. Some exploratory studies using wire-polarizer-based coupling schemes have been described [13,14] but power limitations and system inefficiencies precluded molecular detections. Some success has been documented employing a technique used in cm-wave experiments where radiation is waveguide-coupled into the cavity through an aperture in a spherical end mirror. This approach has reported sensitive detections at 88 GHz [16] however, it requires large optical components and the waveguide feeds limit the application to frequencies <90 GHz. Other success has also been documented [17] at 140 GHz where radiation was injected into an optical cavity via the waveguide attached to an end mirror outfitted with electro-formed coupling holes. Finally, cavity ringdown absorption spectroscopy has shown some promise at 94 GHz. [9]. In this example, the resonator mode-width was narrower than the targeted absorption feature; thus, only broadband attenuation rather than direct rotational lines were observed. The motif common to all these approaches is that the radiation generated from bulky traditional mm-wave sources (e.g., klystron, backward-wave oscillator, and GaAs-based multiplier chain) is injected into the optical cavity through an end mirror element.

By contrast, the spectrometer described herein includes a coupler plate that (1) serves as an end mirror and (2) also hosts waveguide features for the direct injection (detection) of radiation into (out of) the optical cavity. This fundamentally different approach mitigates the loss issues that have plagued some other mm-wave cavity systems while maintaining a compact planar system geometry. A surprising and unexpected feature of the coupler was its relatively high Q factors (narrow linewidths)

REFERENCES

The following references are incorporated by reference herein.

[1] Vision and Voyages for Planetary Science in the Decade 2013-2022, Committee on the Planetary Science Decadal Survey, Space Studies Board Division on Engineering and Physical Sciences, The National Academies Press, Washington, D.C.

[2] H. M. Pickett, R. L. Poynter, E. A. Cohen, M. L. Delitsky, J. C. Pearson, and H. S. P. Muller, J. Quant. Spectrosc. Radiat. Transfer 60, 883-890 (1998).

[3] H. S. P. Müller, F. Schloder, J. Stutzki, and G. Winnewisser, J. Mol. Struct. 742, 215227 (2005).

[4] B. J. Drouin, K. Cooper, R. Dengler, M. Chavez, W. Chun, and T. Crawford, in IEEE Aerospace Conference (IEEE, 2012), pp. 1-4.

[5] C. F. Neese, I. R. Medvedev, G. M. Plummer, A. J. Frank, C. D. Ball, and F. C. De Lucia, IEEE Sens. J. 12, 2565 (2012).

[6] T. J. Balle and W. H. Flygare, Rev. Sci. Instrum. 52, 33 (1981).

[7] N. Gopalsami, A. C. Raptis, and J. Meier, Rev. Sci. Instrum. 73(2), 259-262 (2002).

[8] A. I. Meshkov and F. C. De Lucia, Rev. Sci. Instrum. 76, 083103 (2005).

[9] N. Gopalsami, A. C. Raptis, and J. Meier, "Millimeter-wave cavity ringdown spectroscopy," Rev. Sci. Instrum. 73, 259-262 (2002).

[10] R. N. Clarke and C. B. Rosenberg, "Fabry-Perot and open resonators at microwave and millimeter wave frequencies, 2-300 GHz," J. Phys. E: Sci. Instrum. 15, 9-24 (1982).

[11] A. I. Meshkov and F. C. De Lucia, "Broadband absolute absorption measurements of atmospheric continua with millimeter wave cavity ringdown spectroscopy," Rev. Sci. Instrum. 76, 083103 (2005).

[12] S. Nagarajan, C. F. Neese, and F. C. De Lucia, "Cavity-based medium resolution spectroscopy (CBMRS) in the THz: A bridge between high- and low-resolution techniques for sensor and spectroscopy applications," IEEE Trans. Terahertz Sci. Technol. 7, 233-243 (2017).

[13] R. Braakman and G. A. Blake, "Principles and promise of Fabry-Perot resonators at terahertz frequencies," J. Appl. Phys. 109, 063102 (2011).

[14] B. A. DePrince, B. E. Rocher, A. M. Carroll, and S. L. W. Weaver, "Extending high-finesse cavity techniques to the far-infrared," Rev. Sci. Instrum. 84, 075107 (2013).

[15] A. W. Raymond, "Laser ablation millimeter-wave instrumentation for in situ exploration of the solar system," Ph.D. dissertation (Harvard University, 2018).

[16] D. T. Halfen, V. V. Ilyushin, and L. M. Ziurys, "Interstellar detection of methyl isocyanate $CH_3NCO$ in Sgr B2(N): A link from molecular clouds to comets," Astrophys. J. 812, L5 (2015).

CONCLUSION

This concludes the description of the preferred embodiment of the present invention. The foregoing description of one or more embodiments of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto.

What is claimed is:

1. A coupler for coupling electromagnetic radiation having a wavelength $\lambda$ into a cavity, comprising:
   a mirror including a metal layer having a reflective surface, the metal layer forming a ground plane;
   one or more waveguides for gigahertz or terahertz electromagnetic radiation, each of the waveguides embedded in the metal layer and including:
   two openings in the metal layer exposing a dielectric under the metal layer; and
   a section of the metal layer between the two openings; and
   a plurality of holes in the metal layer disposed along an edge of the openings so as to shape an electric field of electromagnetic radiation outputted from the waveguide to a cavity in a spectrometer coupled to the coupler, the holes exposing the dielectric under the metal layer and the spectrometer determining a composition of a molecule from an interaction of the molecule with the electric field.

2. The coupler of claim 1, wherein the holes are disposed around a perimeter of the waveguide.

3. The coupler of claim 2, wherein the holes are disposed in a hexagonal pattern.

4. The coupler of claim 2, wherein the holes have a diameter or a width in a range of $\lambda/15$-$\lambda/5$ or 200-600 micrometers.

5. The coupler of claim 2, wherein the holes are separated by a distance in a range of $\lambda/5$-$\lambda/2$ or 600-1500 micrometers (distance from a center of one hole to a center of an adjacent hole).

6. The coupler of claim 2, wherein the holes are disposed in 2, 3, or 4 rows.

7. The coupler of claim 2, wherein the openings each have an L shape and the L shapes are positioned symmetrically about the section of the metal layer so as to form mirror images of each other with respect to the section of the metal layer.

8. The coupler of claim 1, wherein the openings have a width in a range of $\lambda/5$-$\lambda/2$.

9. The coupler of claim 1, wherein the openings each have an L shape having a base portion and a back portion.

10. The coupler of claim 9, wherein the base portion has a length in a range of $\lambda/2$-$4\lambda$ or 1-4 mm and the back portion has a length in a range of $3\lambda$-$15\lambda$ or 5-15 mm.

11. The coupler of claim 1, further comprising two of the waveguides embedded in the metal layer, wherein each waveguide is a mirror image of the other waveguide about an axis of symmetry of the metal layer.

12. The coupler of claim 11, wherein:
   the openings each have an L shape having a base portion and a back portion,
   the L shapes in each waveguide are positioned symmetrically about the section of the metal layer so as to form mirror images of each other with respect to the section of the metal layer, and
   a perpendicular distance between the base portions, in one of the waveguides, to the base portions in the other waveguide, is in a range of $\lambda/2$-$3\lambda$.

13. The coupler of claim 12, wherein the reflective surface is rectangular and has sides having a length in a range of $3\lambda$-$15\lambda$.

14. The coupler of claim 12, wherein:
   the reflective surface is rectangular and has a first side opposite a second side, the first side and the second side each having a length in a range of $3\lambda$-$15\lambda$,
   the waveguides include a first waveguide and a second waveguide,
   the openings and the section in the first waveguide extend to the first side, and
   the openings and the section in the second waveguide extend to the second side.

15. The coupler of claim 1, wherein the waveguides each comprise a stripline including the section of the metal layer between two sections of the ground plane.

16. The coupler of claim 1, wherein:
the coupler coupled to a second mirror forms the cavity confining the electromagnetic radiation and generating modes of the electromagnetic radiation in the cavity when the electromagnetic radiation is coupled into the cavity through the coupler,
the modes comprise peaks and nodes of a cavity electric field evenly spaced along the cavity's longitudinal axis (cavity axis), and
the cavity electric field is symmetrically distributed in at least one direction perpendicular to the cavity axis.

17. The coupler of claim 1, wherein:
the coupler coupled to a second mirror forms the cavity confining the electromagnetic radiation and generating modes of the electromagnetic radiation in the cavity when the electromagnetic radiation is coupled into the cavity through the coupler,
the modes comprise peaks and nodes of a cavity electric field spaced along the cavity's longitudinal axis (cavity axis),
the cavity electric field at a first point and a second point symmetrically positioned on either side of the cavity axis are the same to within 10%.

18. The coupler of claim 17, wherein the first point and the second point are each at a same distance in a range of $\lambda$-$3\lambda$ from the cavity axis.

19. A spectrometer comprising the cavity of claim 12, comprising:
a transmitter coupled to the waveguide, wherein the transmitter transmits an electric field to the waveguide, wherein the electric field is transmitted along the waveguide and generates the electromagnetic radiation outputted from the coupler into the cavity;
a receiver coupled to the waveguide, the waveguide receiving an output electric field transmitted along the waveguide in response to a presence of the molecule in the cavity and interacting with the cavity electrical field of the electromagnetic radiation; and
a computer coupled to the receiver determining the composition of the molecule from the output electric field.

20. The spectrometer of claim 19, wherein:
the waveguides comprise a first waveguide and a second waveguide,
the openings and the section in the first waveguide extend to a side of the reflective surface, the spectrometer further comprising:

the transmitter including:
a first output electrically connected to the section at the side; and
a second output electrically connected to the ground plane at the side; and wherein the first and second outputs apply an electrical field across the section and the ground plane; and
a receiver including:
a first input electrically connected to the section at the side; and
a second input electrically connected to the ground plane;
wherein the first and second inputs receive the output electrical field applied across the section and the ground plane in response to the molecule in the cavity interacting with the cavity electrical field.

21. A coupler for coupling electromagnetic radiation having a wavelength $\lambda$,
comprising:
a mirror including a metal layer having a reflective surface, the metal layer forming a ground plane;
one or more waveguides for gigahertz or terahertz electromagnetic radiation, each of the waveguides embedded in the metal layer and including:
two openings in the metal layer exposing a dielectric under the metal layer;
a section of the metal layer between the two openings; and
a plurality of holes in the metal layer disposed along an edge of the openings:
wherein:
the holes have a diameter or a width in a range of $\lambda/15$-$\lambda/5$,
the holes are separated by a distance in a range of $\lambda/5$-$\lambda/2$, wherein the distance is from a center of one hole to a center of an adjacent hole,
the openings have a width in a range of $\lambda/5$-$\lambda/2$, and
the openings each have an L shape having a base portion and a back portion,
wherein the base portion has a length in a range of $\lambda/2$-$4\lambda$ and the back portion has a length in a range of $3\lambda$-$15\lambda$ or 5-15 mm.

* * * * *